(12) United States Patent
Akahori

(10) Patent No.: US 8,804,912 B2
(45) Date of Patent: Aug. 12, 2014

(54) RADIOGRAPHIC IMAGING APPARATUS, METHOD AND PROGRAM

(75) Inventor: Sadato Akahori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 391 days.

(21) Appl. No.: 13/184,969

(22) Filed: Jul. 18, 2011

(65) Prior Publication Data

US 2012/0014498 A1  Jan. 19, 2012

(30) Foreign Application Priority Data

Jul. 16, 2010 (JP) .................................. 2010-161169

(51) Int. Cl.
*H05G 1/26* (2006.01)
*A61B 6/08* (2006.01)
*A61B 6/00* (2006.01)
*A61B 6/02* (2006.01)

(52) U.S. Cl.
CPC .................. *A61B 6/025* (2013.01); *A61B 6/547* (2013.01); *A61B 6/583* (2013.01); *A61B 6/587* (2013.01)
USPC .............. 378/163; 378/21; 378/165; 378/205

(58) Field of Classification Search
USPC ................ 378/4–20, 56, 62, 91, 95, 98, 98.8, 378/98.12, 162, 163, 165, 166, 204, 205, 378/207, 901; 382/128, 130, 131, 216, 287, 382/291
See application file for complete search history.

(56) References Cited

U.S. PATENT DOCUMENTS

| | | | |
|---|---|---|---|
| 5,276,613 A * | 1/1994 | Schlumberger | 378/4 |
| 6,196,715 B1 | 3/2001 | Nambu et al. | |
| 6,206,566 B1 * | 3/2001 | Schuetz | 378/205 |
| 6,379,043 B1 * | 4/2002 | Zylka et al. | 378/207 |
| 6,671,349 B1 * | 12/2003 | Griffith | 378/163 |
| 6,888,924 B2 * | 5/2005 | Claus et al. | 378/163 |
| 6,960,020 B2 | 11/2005 | Lai | |

(Continued)

FOREIGN PATENT DOCUMENTS

JP  10-295680 A  11/1998
JP  2003-024321 A  1/2003

(Continued)

OTHER PUBLICATIONS

European Search Report issued in European Patent Application No. 11174090.8-2319, dated Oct. 19, 2011.

(Continued)

*Primary Examiner* — Anastasia Midkiff
(74) *Attorney, Agent, or Firm* — Sughrue Mion, PLLC

(57) ABSTRACT

A radiographic imaging apparatus includes: a radiation source for applying radiation to a subject and at least one marker; a detecting unit for detecting the radiation transmitted through the subject; and an image obtaining unit for moving the radiation source relative to the detecting means, applying the radiation to the subject from a plurality of radiation source positions provided by the movement of the radiation source, and obtaining a plurality of images corresponding respectively to the radiation source positions. The apparatus further includes a radiation source position obtaining unit for obtaining positional information of each radiation source position of interest relative to a reference radiation source position among the radiation source positions based on at least one marker image contained in each of a reference image obtained with the reference radiation source position and an image of interest obtained with the radiation source position of interest.

5 Claims, 7 Drawing Sheets

(56) References Cited

U.S. PATENT DOCUMENTS

| | | | |
|---|---|---|---|
| 7,147,373 B2 * | 12/2006 | Cho et al. | 378/207 |
| 2002/0131559 A1 | 9/2002 | Launay et al. | |
| 2004/0252811 A1 | 12/2004 | Morita et al. | |
| 2004/0264648 A1 | 12/2004 | Claus et al. | |
| 2007/0127622 A1 * | 6/2007 | Main et al. | 378/64 |
| 2007/0165922 A1 * | 7/2007 | Webber et al. | 382/128 |
| 2008/0186311 A1 | 8/2008 | Claus | |
| 2010/0310044 A1 * | 12/2010 | Manak et al. | 378/62 |

FOREIGN PATENT DOCUMENTS

| | | |
|---|---|---|
| JP | 2005-021345 A | 1/2005 |
| JP | 2005-021675 A | 1/2005 |
| JP | 2006-326175 A | 12/2006 |
| JP | 2008-188426 A | 8/2008 |
| WO | 03/020114 A2 | 3/2003 |

OTHER PUBLICATIONS

European Office Action; Application No. 11 174090.8-1660; Apr. 3, 2013.

Office Action dated Dec. 3, 2013, issued by the Japanese Patent and Trade Mark Office in counterpart Japanese Patent Application No. 2010-161169.

* cited by examiner

RADIOGRAPHIC IMAGING APPARATUS, METHOD AND PROGRAM

BACKGROUND OF THE INVENTION

1. Field of the Invention

The present invention relates to radiographic imaging apparatus, method and program for obtaining a plurality of images at a plurality of radiation source positions, to achieve, for example, tomosynthesis imaging to generate tomographic images.

2. Description of the Related Art

In recent years, tomosynthesis imaging has been proposed with respect to X-ray imaging apparatuses to more closely observe an affected part of the body. In the tomosynthesis imaging, imaging operations are carried out by applying the X-ray to a subject from different angles with moving the X-ray tube, and the thus obtained images are added up to provide an image in which a desired slice is emphasized. In the tomosynthesis imaging, the X-ray tube may be moved in parallel with the X-ray detector or may be moved in a circular or ellipsoidal arc, depending on characteristics of the imaging apparatus and necessary tomographic images, to obtain images of the subject imaged with different irradiation angles, and these images are reconstructed to generate tomographic images.

In the case where such tomosynthesis imaging is performed, it is necessary to align the images obtained through the imaging operations to reconstruct the images. For this purpose, a technique which involves calculating the positions of the X-ray tube during the imaging operations (which will hereinafter be referred to as "radiation source positions") by equally dividing the range of movement of the X-ray tube by the number of imaging operations (number of shots), and reconstructing the images with using information of the calculated radiation source positions has been proposed.

This technique, however, has difficulty in accurately moving the X-ray tube to the calculated radiation source positions due to influences of vibration during imaging, mechanical misalignment, etc., and therefore the radiation source positions during imaging are displaced from the calculated radiation source positions. Due to this displacement, it is impossible to achieve accurate alignment of projection positions of the object, resulting in degradation of image quality of the tomographic images.

Therefore, it is practiced during tomosynthesis imaging to place markers on a subject or on an imaging table on which the subject is placed, and imaging the markers together with the subject to obtain images containing marker images (see Japanese Unexamined Patent Publication No. 2005-021345, U.S. Patent Application Publication No. 20040252811, and U.S. Pat. No. 6,196,715, which will hereinafter be referred to as Patent Documents 1 to 3). According to the techniques disclosed in Patent Documents 1 to 3, an accurate radiation source position for each image is calculated with using positional information of a phantom containing the markers, and the images are reconstructed with using the calculated radiation source positions to eliminate influence of the displacement of the radiation source positions. Further, a technique to simultaneously estimate a displacement parameter of a support position and an imaging position has been proposed with taking displacement of the position of the support containing a plurality of markers into account (see U.S. Patent Application Publication No. 20020131559, which will hereinafter be referred to as Patent Document 4).

On the other hand, a technique to correct for positional displacement between a plurality of images with using amounts of shift of positions of marker images between the images, without using positional information of the markers, has been proposed (see U.S. Pat. No. 6,960,020, which will hereinafter be referred to as Patent Document 5). Now, the technique disclosed in Patent Document 5 is described.

FIG. 9 is a diagram for explaining how alignment is achieved in the technique disclosed in Patent Document 5. In FIG. 9, a direction parallel to the movement path of the X-ray tube is referred to as the x-direction, a direction perpendicular to the movement path of the X-ray tube is referred to as the z-direction, and a direction perpendicular to the plane of the drawing is referred to as the y-direction. As shown in FIG. 9, when the X-ray tube is moved from a radiation source position S11 to a radiation source position S12 by an amount $\Delta xs$, a marker image of a marker M0 placed on a imaging table top 104 is shifted by an amount $\Delta xm$, and a projection position of an object T0, which is the object of reconstruction, in a subject 102 is shifted by an amount $\Delta xt$. Assuming here that a distance between the X-ray tube and the detection plane of a detector 114 (i.e., a radiation source distance) is sz, a distance between the detection plane of the detector 114 and a plane in which the object T0 is present is tz, and a distance between the detection plane of the detector 114 and the top surface of the imaging table top 104 is mz, then, the amount of movement $\Delta xs$ of the radiation source position is expressed by Equation (1) below with using the amount of shift $\Delta xm$ of the marker image, the radiation source distance sz and the distance mz:

$$\Delta xs = \Delta xm \times (sz-mz)/mz \quad (1)$$

Further, the amount of shift $\Delta xt$ of the projection position of the object is expressed by Equation (2) below with using the amount of movement $\Delta xs$ of the radiation source position, the radiation source distance sz and the distance tz:

$$\Delta xt = \Delta xs \times tz/(sz-tz) \quad (2)$$

According to Equations (1) and (2), the amount of shift $\Delta xt$ of the projection position of the object is expressed by Equation (3) below with using the amount of shift $\Delta xm$ of the marker image, the radiation source distance sz, the distance mz and the distance tz:

$$\Delta xt = \Delta xm \times (tz/mz) \times (sz-mz)/(sz-tz) \quad (3)$$

By calculating the amount of shift $\Delta xt$ of each projection position of the object in this manner, alignment of the projection positions of the object in the images can be achieved to reconstruct the tomographic images.

However, the techniques disclosed in Patent Document 1 to 3 use the positions of the markers as known information to calculate the radiation source positions. Therefore, in order to find accurate radiation source positions, it is necessary that the phantom containing the markers is accurately made, with the markers being accurately placed at predetermined positions in the phantom. Although accurate positional information of the markers can be obtained by fixing the markers to a fixture, such a fixture is large to some extent, and thus is not suitable for imaging various subjects. Further, use of a marker fixture limits positions of the markers, and therefore, in the case where a radiation field aperture is used during imaging, it may be impossible to position the markers within the radiation field. On the other hand, the technique disclosed in Patent Document 4 uses relative positions of the markers in the support as known information, and it is necessary to accurately position the markers in the support.

Further, the technique disclosed in Patent Document 5 assumes that the movement path of the X-ray tube is always parallel to the detection plane of the detector. Therefore, accurate alignment cannot be achieved when the radiation source positions for obtaining the images are not on a movement path that is parallel to the detection plane of the detector.

SUMMARY OF THE INVENTION

In view of the above-described circumstances, the present invention is directed to providing accurate alignment of images when a plurality of images are obtained with a plurality of radiation source positions, such as in tomosynthesis imaging.

An aspect of the radiographic imaging apparatus according to the invention is a radiographic imaging apparatus including: a radiation source for applying radiation to a subject and at least one marker; detecting means for detecting the radiation transmitted through the subject; image obtaining means for moving the radiation source relative to the detecting means, applying the radiation to the subject from a plurality of radiation source positions provided by the movement of the radiation source, and obtaining a plurality of images corresponding respectively to the radiation source positions; and radiation source position obtaining means for obtaining positional information of each radiation source position of interest relative to a reference radiation source position, the radiation source position of interest being one of the radiation source positions other than the reference radiation source position among the radiation source positions, based on at least one marker image contained in each of a reference image obtained with the reference radiation source position and an image of interest obtained with the radiation source position of interest.

The description "moving the radiation source relative to the detecting means" herein includes the case where the detecting means is fixed and only the radiation source is moved and the case where both the detecting means and the radiation source are moved synchronously.

In the radiographic imaging apparatus according to the invention, the radiation source position obtaining means may obtain the positional information of each radiation source position of interest based on a three-dimensional positional relationship among a position of the at least one marker image contained in each of the reference image and the image of interest, the reference radiation source position and the radiation source position of interest.

In the radiographic imaging apparatus according to the invention, the radiation source position obtaining means may obtain the positional information of each radiation source position of interest by determining an optimal solution of the positional information of the radiation source position of interest to minimize an error between a position of the at least one marker image contained in each of the reference image and the image of interest and a projection position of the marker image calculated from a relationship among the reference radiation source position, the radiation source position of interest and a position of the marker.

In this case, the radiation source position obtaining means may determine the optimal solution of the positional information of each radiation source position of interest by repeating optimization of the positional information of the radiation source position of interest and optimization of positional information of the marker.

The radiographic imaging apparatus according to the invention may further include image reconstructing means for generating a tomographic image of the subject with using the reference radiation source position and the positional information of each radiation source position of interest.

An aspect of the radiographic imaging method according to the invention is a radiographic imaging method for use with a radiographic imaging apparatus including a radiation source for applying radiation to a subject and at least one marker, detecting means for detecting the radiation transmitted through the subject, and image obtaining means for moving the radiation source relative to the detecting means, applying the radiation to the subject from a plurality of radiation source positions provided by the movement of the radiation source, and obtaining a plurality of images corresponding respectively to the radiation source positions, the method including: obtaining positional information of each radiation source position of interest relative to a reference radiation source position, the radiation source position of interest being one of the radiation source positions other than the reference radiation source position among the radiation source positions, based on at least one marker image contained in each of a reference image obtained with the reference radiation source position and an image of interest obtained with the radiation source position of interest.

The radiographic imaging method according to the invention may be provided in the form of a program for causing a computer to carry out the radiographic imaging method.

According to the invention, the positional information of each radiation source position of interest relative to the reference radiation source position among the radiation source positions is obtained based on at least one marker image contained in each of the reference image obtained with the reference radiation source position and the image of interest obtained at the radiation source position of interest. Therefore, even when the radiation source positions are displaced from a predetermined movement path, the positional information of each radiation source position of interest relative to the reference imaging position can be obtained. Further, when the positional information is calculated, it is not necessary to use the positional information of the at least one marker. In particular, even in the case where two or more markers are used, it is not necessary to use information about the relationship between the markers. Therefore, the markers can be freely positioned during imaging, thereby increasing freedom of imaging.

In the case where the positional information of each radiation source position of interest is obtained based on a three-dimensional positional relationship among a position of the at least one marker image contained in each of the reference image and the image of interest, the reference radiation source position and the radiation source position of interest, the positional information of the radiation source position of interest relative to the reference radiation source position can be obtained by a relatively simple calculation.

In the case where the positional information of each radiation source position of interest is obtained by determining an optimal solution of the positional information of the radiation source position of interest to minimize an error between a position of the at least one marker image contained in each of the reference image and the image of interest and a projection position of the marker image calculated from a relationship among the reference radiation source position, the radiation source position of interest and a position of the marker, not only the radiation source position of interest but also the positional information of the marker can be obtained. Therefore, even if some of the markers are erroneously detected or fail to be detected, the position coordinates of the markers can be obtained in a relatively stable manner. Further, in particular, in the case where two or markers are used for alignment between the reference image and the other images, the alignment can be achieved even if the heights of positions of the markers are not the same.

In the case where the optimal solution of the positional information of each radiation source position of interest is determined by repeating optimization of the positional information of the radiation source position of interest and optimization of positional information of the marker, efficient calculation of the position coordinates of each radiation source position of interest can be achieved.

In the case where the tomographic image of the subject is generated with using the reference radiation source position and the positional information of each radiation source position of interest, influence of mechanical misalignment during imaging can be eliminated, thereby providing a high quality tomographic image.

DESCRIPTION OF THE PREFERRED
EMBODIMENTS

Figure 1:
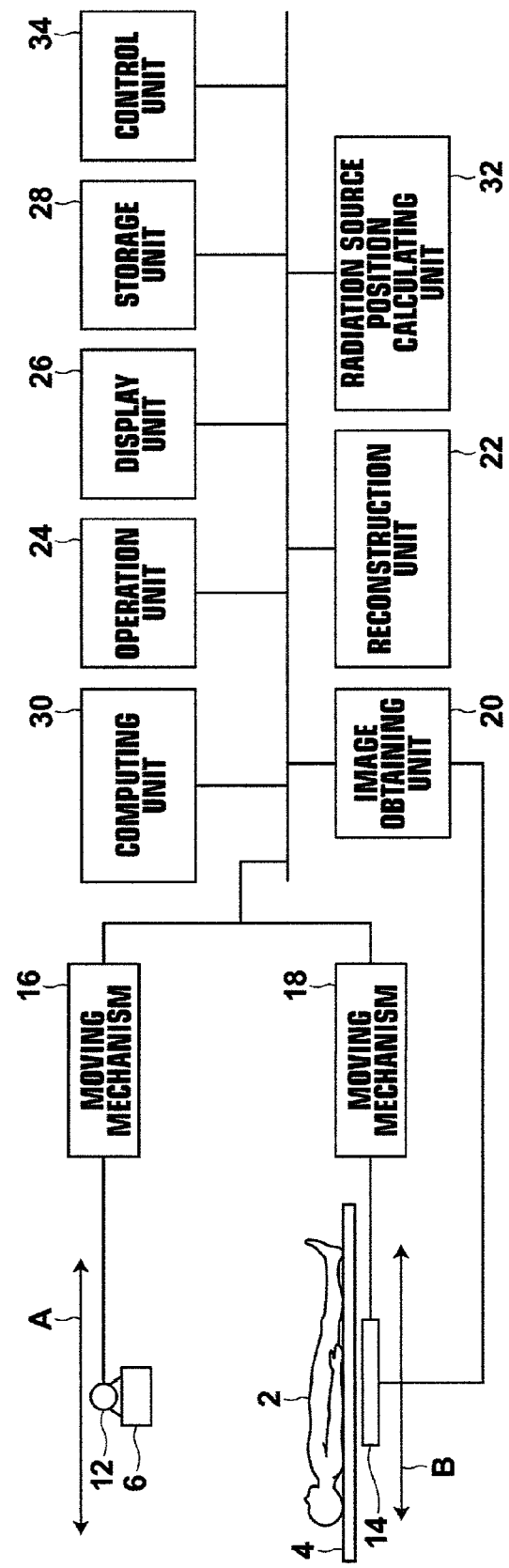
FIG. 1 is a schematic diagram illustrating an X-ray imaging apparatus, to which a radiographic imaging apparatus according to a first embodiment of the preset invention is applied.

Hereinafter, embodiments of the present invention will be described with reference to the drawings. FIG. 1 is a schematic diagram illustrating an X-ray imaging apparatus, to which a radiographic imaging apparatus according to a first embodiment of the invention is applied. As shown in FIG. 1, the X-ray imaging apparatus 10 according to the first embodiment is used to perform tomosynthesis imaging, and includes an X-ray tube 12 and a flat panel X-ray detector (which will hereinafter be referred simply to as "detector") 14. The X-ray tube 12 is moved by a moving mechanism 16 along a straight line or a circular arc, and applies an X-ray from a plurality of positions along the movement path to a subject 2 on an imaging table top 4. In this embodiment, the X-ray tube 12 is moved in the direction of arrow A along a straight line. The X-ray dose applied to the subject 2 is controlled by a control unit, which will be described later, to be a predetermined dose.

Further, a collimator (radiation field aperture) 6 is connected to the X-ray tube 12 so that the operator can set the range of the X-ray (exposure range) applied to the subject 2. It should be noted that, when the exposure range is set with using the collimator 6, visible light, in place of the X-ray, is applied to the subject 2 through the collimator 6. The visible light is emitted from a radiation field lamp (not shown) provided at the collimator 6. Thus, the operator can set the exposure range of the X-ray by adjusting the range of the visible light applied to the subject 2 with using the collimator 6. Further, in this embodiment, markers are positioned on the imaging table top 4, as will be described later, and imaging operations are carried out to obtain a plurality of images containing the markers together with the subject 2.

The detector 14 is disposed to face the X-ray tube 1 via the imaging table top 4, on which the subject 2 is placed, to detect the X-ray transmitted through the subject 2. The detector 14 is moved along a straight line or a circular arc by the moving mechanism 18, as necessary, and detects the X-ray transmitted through the subject 2 at a plurality of positions along the movement path. In this embodiment, the detector 14 is moved in the direction of arrow B along a straight line.

The X-ray imaging apparatus 10 further includes an image obtaining unit 20 and a reconstruction unit 22. The image obtaining unit 20 causes the X-ray tube 12 to be moved along the straight line, applies the X-ray to the subject 2 from a plurality of radiation source positions, which are provided by the movement of the X-ray tube 12, and detects the X-ray transmitted through the subject 2 with the detector 14 to obtain a plurality of images at the plurality of radiation source positions while the X-ray tube 12 is moved. The reconstruction unit 22 reconstructs the images obtained by the image obtaining unit 20 to generate a tomographic image showing a desired slice of the subject 2. Now, a method of reconstructing the tomographic images is described.

Figure 2:
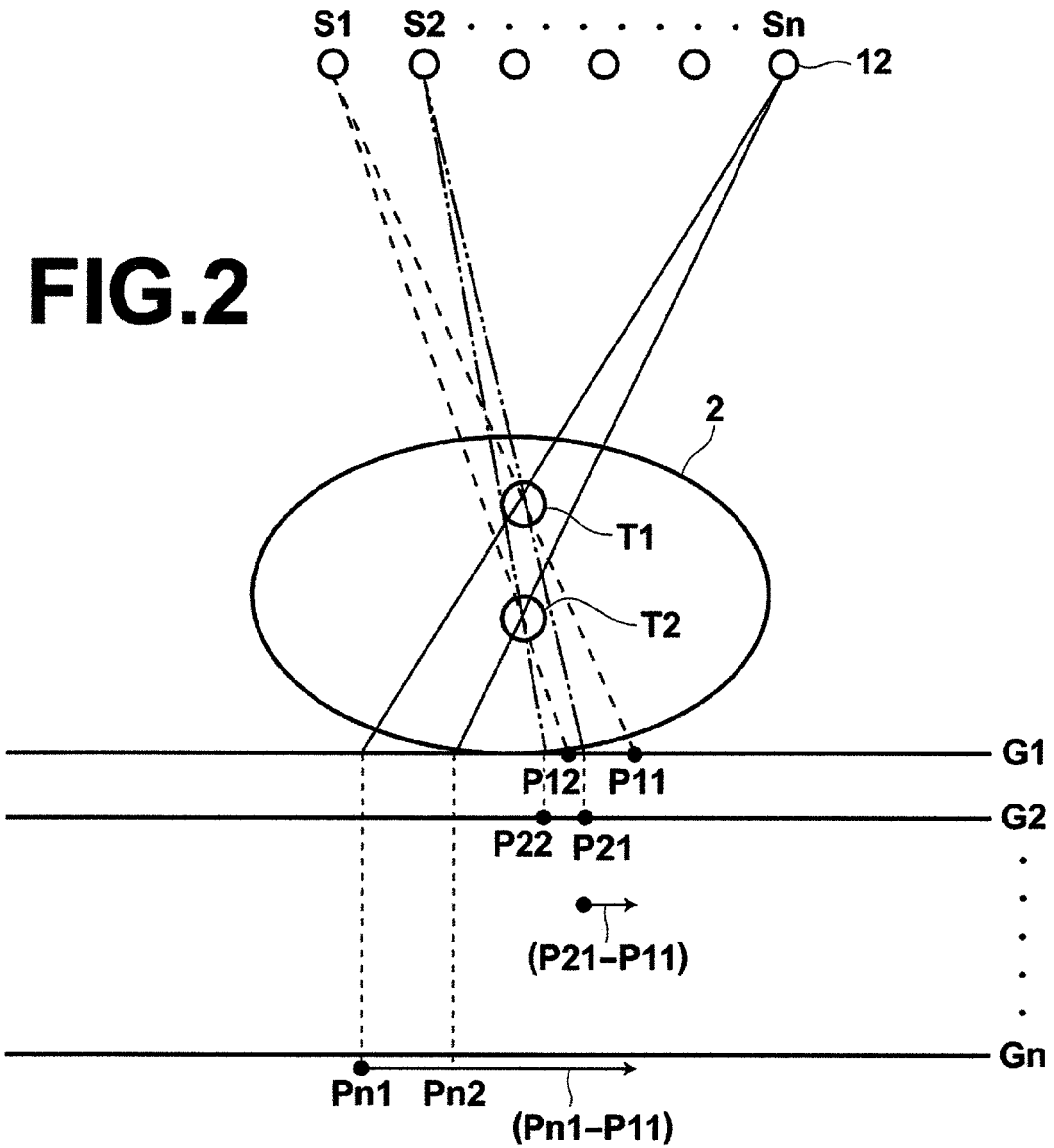
FIG. 2 is a diagram for explaining tomosynthesis imaging.

As shown in FIG. 2, it is assumed here that the subject 2 is imaged from different irradiation angles with moving the X-ray tube 12 to positions S1, S2, . . . , and Sn, and image G1, G2, . . . , and Gn are obtained. For example, when objects (T1, T2) at different depths are projected from the radiation source position S1, projection images of the objects (T1, T2) are formed at positions P11 and P12 on the image G1. When the objects (T1, T2) are projected from the radiation source position S2, projection images of the objects (T1, T2) are formed at positions P21 and P22 on the image G2. In this manner, by repeating projection from the different radiation source position 51, S2, . . . , and Sn, projection images of the object T1 are formed at positions P11, P21, . . . , and Pn1 and projection images of the object T2 are formed at positions P12, P22, . . . , and Pn2 correspondingly to the radiation source positions.

If it is desired to emphasize the slice where the object T1 is present, the images are aligned such that the image G2 is shifted by an amount of P21-P11, the image G3 is shifted by an amount of P31-P11, . . . , and the image Gn is shifted by an amount of Pn1-P11), and then the images are added up to provide a tomographic image in which structures in the slice at the depth of the object T1 are emphasized. If it is desired to emphasize the slice where the object T2 is present, the images are aligned such that the image G2 is shifted by an amount of P22-P12, the image G3 is shifted by an amount of P32-P12, . . . , and the image Gn is shifted by an amount of Pn2-P12, and then the images are added up. By adding the images G1, G2, . . . , and Gn with aligning the images depending on the position of the necessary slice in this manner, an image in which a tomographic image at a desired position is emphasized can be obtained. It should be noted that, since the markers are positioned on the imaging table top 4 and the images are obtained such that the markers are imaged in this embodiment, the images contain the marker images. Therefore, the alignment of the images G1, G2, . . . , and Gn is achieved with using the marker images.

The X-ray imaging apparatus 10 further includes an operation unit 24, a display unit 26 and a storage unit 28. The operation unit 24 includes a keyboard, a mouse or a touch panel type input device, and receives operation of the X-ray imaging apparatus 10 by the operator. The operation unit 24 also receives inputs of various information, such as imaging conditions, necessary for carrying out the tomosynthesis imaging and instructions to correct the information. In this embodiment, the units of the X-ray imaging apparatus 10 operate according to the information inputted by the operator via the operation unit 24. The display unit 26 is a display device, such as a liquid crystal monitor, and displays the images obtained by the image obtaining unit 20 and the tomographic images reconstructed by the reconstruction unit 22, as well as messages necessary for operation by the operator. The display unit 26 may include a speaker to output a sound. The storage unit 28 stores various parameters for setting imaging conditions, which are necessary for operating the X-ray imaging apparatus 10, etc. With respect to these parameters, standard values for each part to be imaged are stored in the storage unit 28. These values are corrected, as necessary, according to instructions by the operator inputted via the operation unit 24.

The parameters for setting the imaging conditions may include a reference plane, a slice angle, a radiation source distance, the number of shots, a shot interval, a tube voltage and a tube current of the X-ray tube 12, and an X-ray exposure time, for example. It should be noted that, among these parameters, values of the number of shots, the shot interval, the tube voltage and the tube current of the X-ray tube 12, and the X-ray exposure time may be used as the imaging conditions without any conversion.

Figure 3:
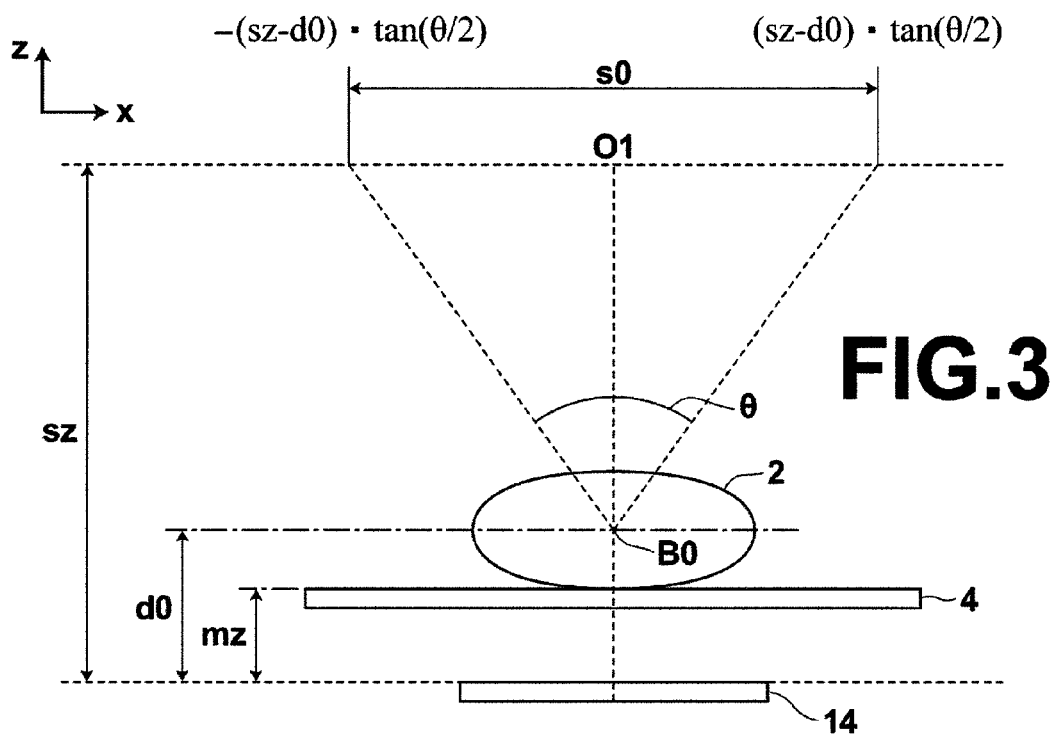
FIG. 3 is a diagram for explaining various parameters.

FIG. 3 is a diagram for explaining the various parameters. The reference plane defines a range in which tomographic images are obtained, and may, for example, be the top surface of the imaging table top 4, the detection plane of the detector 14 or any slice of the subject 2. In FIG. 3, a plane that divides the thickness of the subject 2 in halves (which will hereinafter be referred to as "center plane") is used as the reference plane. The slice angle is an angle formed between lines extending from a reference point B0 on the reference plane toward two ends of the range of movement of the X-ray tube 12. Since the detection plane of the detector 14 is parallel to the movement path of the X-ray tube 12, the radiation source distance is the shortest distance between the movement path of the X-ray tube 12 and the detection plane of the detector 14.

The number of shots is the number of imaging operations carried out while the X-ray tube 12 is moved from one end to the other end in the range of the slice angle. The shot interval is a time interval between shots.

It should be noted that, in the following description, it is assumed that the range of movement of the X-ray tube 12 is s0, the slice angle is θ, and the distance between the detection plane of the detector 14 and the reference plane (i.e., the center plane of the subject 2) is d0. Further, as the predetermined reference point B0 on the reference plane, the intersection point between the reference plane and a perpendicular line passing through the centroid of the detector 14 is used.

The X-ray imaging apparatus 10 further includes a computing unit 30. The computing unit 30 calculates the imaging conditions, such as the range of movement of the X-ray tube 12, according to the parameters stored in the storage unit 28.

Referring to the relationships shown in FIG. 3, the range of movement s0 of the X-ray tube 12 can be calculated from the radiation source distance sz, the distance d0 and the slice angle θ. That is, assuming that the intersection point between the movement path of the X-ray tube 12 and the perpendicular line passing through the reference point B0 is the origin O1, the distance between the reference plane and the X-ray tube 12 is sz-d0. Therefore, the computing unit 30 calculates the range of movement s0 of the X-ray tube 12 as: $-(sz-d0)\cdot\tan(\theta/2)$ to $(sz-d0)\cdot\tan(\theta/2)$. With this, positions of opposite ends of the calculated range of movement s0 are determined.

Further, the computing unit 30 calculates the position of the X-ray tube 12 in each imaging operation (which will hereinafter be referred to as "radiation source position") by equally dividing the range of movement s0 of the X-ray tube 12 by the number of shots. Thus, the radiation source positions S1, S2, . . . , and Sn of the X-ray tube 12, as shown in FIG. 2, are calculated.

Further, the computing unit 30 calculates an imaging time and a radiation source traveling speed as the imaging conditions. The imaging time is calculated by: the number of shots× the shot interval. The radiation source traveling speed is calculated by: the range of movement s0/the imaging time.

The X-ray tube 12 actually moves with a mechanical error, not exactly along the calculated movement path parallel to the imaging table top 4. In this case, the radiation source positions are also displaced from the radiation source positions calculated by the computing unit 30. The above-described Equation (3) for calculating the amount of shift of the projection position of the object in the subject 2 assumes that the X-ray tube 12 moves parallel to the imaging table top 4 and the imaging operations are carried out with the radiation source positions calculated by the computing unit 30. Therefore, if the X-ray tube 12 does not move parallel to the imaging table top 4 and the imaging operations are carried out with radiation source positions displaced from the radiation source positions calculated by the computing unit 30, it is impossible to achieve accurate alignment of the projection positions of the object by using the amounts of shift Δxt of the projection positions of the object calculated according to Equation (3). In order to solve this problem, the X-ray imaging apparatus 10 according to this embodiment is provided with a radiation source position calculating unit 32 for calculating, as positional information, position coordinates of the actual radiation source positions of the X-ray tube 12 with using the marker images contained in the images.

The radiation source position calculating unit 32 sets one of the radiation source positions as a reference radiation source position, and sets an image obtained with the reference radiation source position as a reference image. The reference radiation source position may, for example, be a radiation source position with which a first imaging operation is carried out. Then, the radiation source position calculating unit 32 detects marker images of markers M1 to M4 from each of images obtained through tomosynthesis imaging, and uses positional information of the detected marker images (coordinates of the center position of each marker image) to calculate the positional information of each radiation source position other than the reference radiation source position, namely, relative position coordinates of each radiation source position relative to the reference radiation source position.

Figure 4:
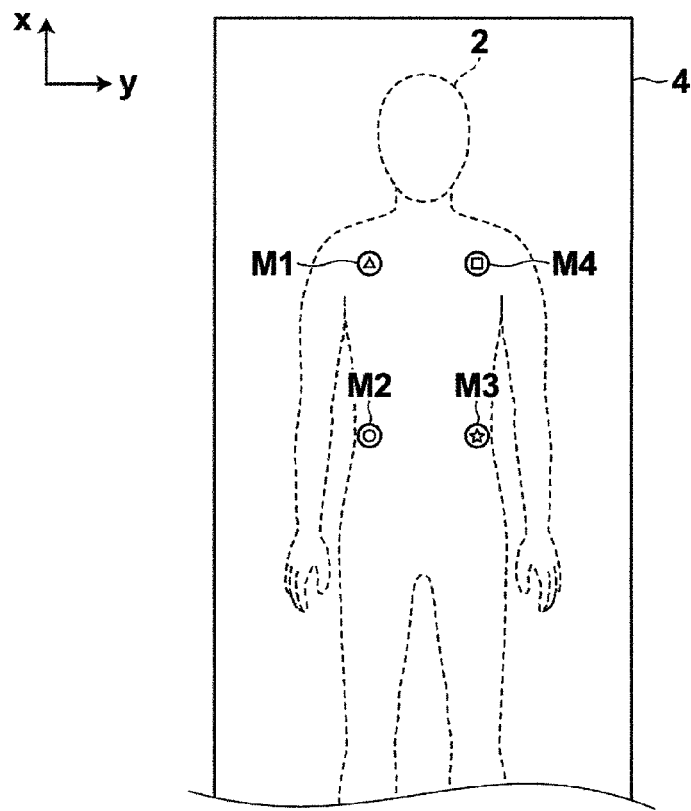
FIG. 4 is a plan view of an imaging table top for explaining markers used in embodiments of the invention and positioning of the markers.

FIG. 4 is a plan view of the imaging table top for explaining the markers used in this embodiment and positioning of the markers. As shown in FIG. 4, in this embodiment, the four circular markers M1 to M4 are used, and the operator positions the four markers M1 to M4 on the imaging table top 4 such that the markers M1 to M4 overlap with the subject 2 in directions in which the X-ray is applied. The markers M1 to M4 are made of a material having high X-ray absorption, such as lead. The size of the markers M1 to M4 is about 1 cm, and each includes a hole having a unique shape. The different shapes of the holes allow recognition of each of the four markers M1 to M4 contained in the images. In FIG. 4, the markers M1 to M4 are enlarged for the purpose of explanation. The shape of the markers is not limited to circle, and may be any known shape. The number of the markers is not limited to four, and may be any number of two or more. Further, the markers may not be of different types, and the same type of markers may be used.

The radiation source position calculating unit 32 detects the marker images by applying a known pattern recognition process to the reference image to obtain the positional information of the marker images (specifically, the position coordinates of the marker images). Further, the radiation source position calculating unit 32 detects the marker images from each image of interest with using the marker images detected from the reference image as a template and obtains the position coordinates of the marker images. Since each of the four markers M1 to M4 used in this embodiment has the unique hole, the marker image of each of the four markers M1 to M4 can be recognized independently. In this case, a computing time for detecting the marker images can be reduced by detecting the positions of the marker images in the image of interest in areas in the vicinity of positions corresponding to the detected positions of the marker images in the reference image. Then, the radiation source position calculating unit 32 calculates each radiation source position with using the position coordinates of the marker images in each image of interest.

Figure 5:
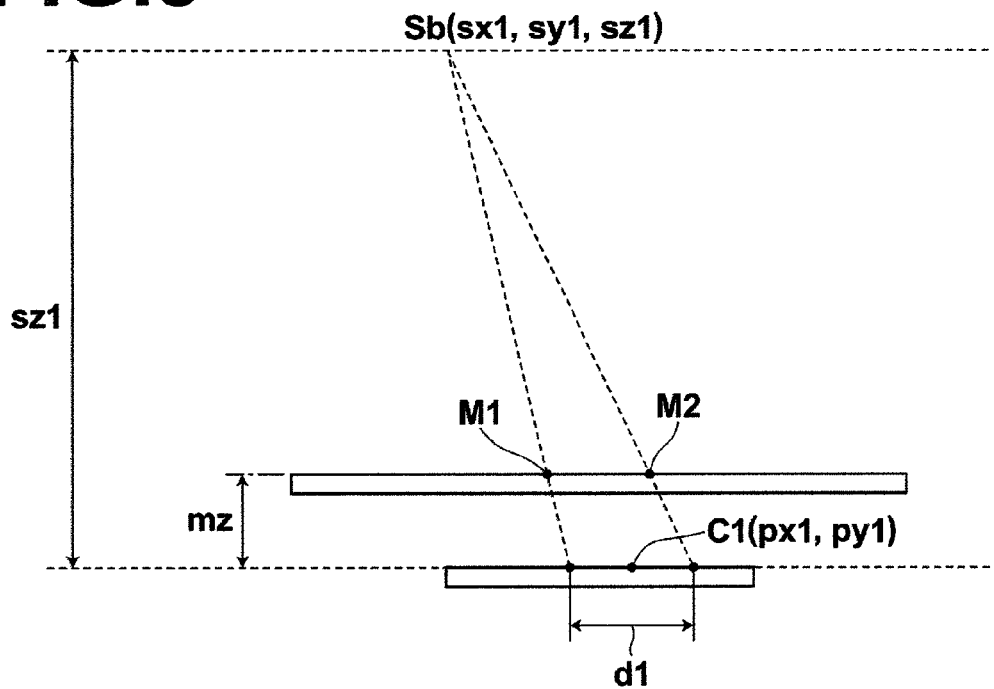
FIG. 5 is a diagram for explaining how radiation source positions are calculated.
Figure 6:
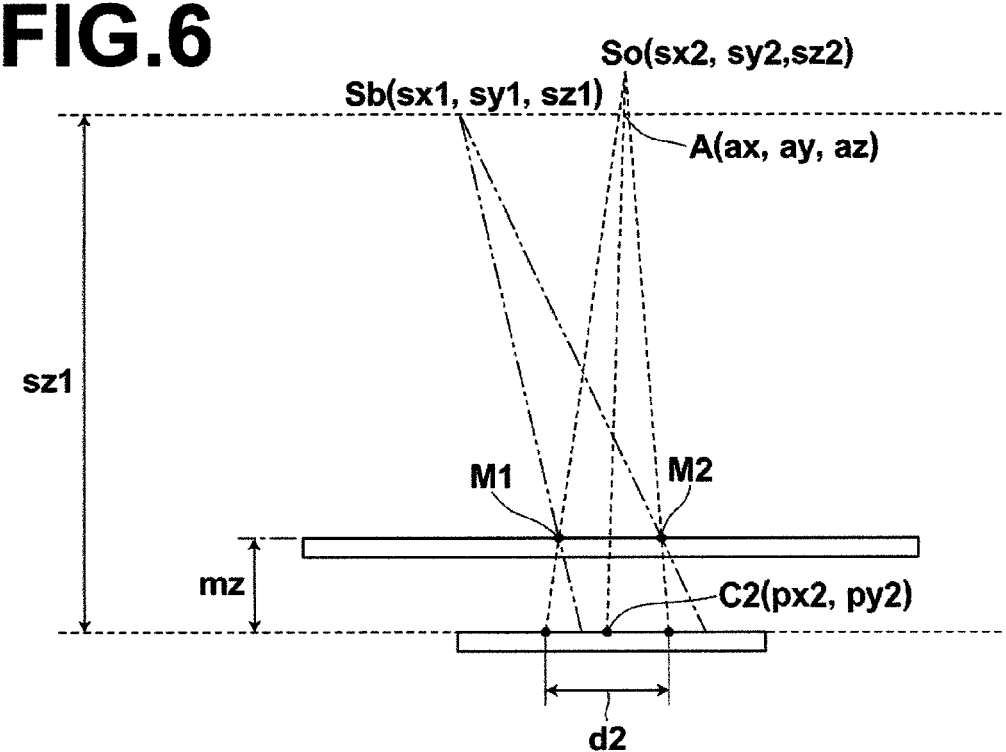
FIG. 6 is a diagram for explaining how radiation source positions are calculated.

FIGS. 5 and 6 are diagrams for explaining how the radiation source positions are calculated. In FIGS. 5 and 6, the reference radiation source position is denoted by "Sb", the position coordinates of the reference radiation source position Sb are denoted by "(sx1,sy1,sz1)", the radiation source position of interest, which is the object of the position calculation, is denoted by "So", and the position coordinates of the radiation source position of interest are denoted by "(sx2,sy2,sz2)". In this explanation, it is assumed that imaging operations are carried out with using two markers M1 and M2. Further, as shown in FIG. 5, position coordinates of a midpoint C1 between marker images of the markers M1 and M2 in an image (which is the reference image) obtained when the X-ray tube 12 is at the reference radiation source position Sb are denoted by "(px1,py1)", and a distance between the marker images of the markers M1 and M2 is denoted by "d1". Further, as shown in FIG. 6, position coordinates of a midpoint C2 between marker images of the markers M1 and M2 in an image (which is the image of interest) obtained when the X-ray tube 12 is at the radiation source position of interest So are denoted by "(px2,py2)", and a distance between the marker images of the markers M1 and M2 is denoted by "d2".

Assuming, with reference to FIG. 6, that an intersection point where a segment connecting the midpoint C2 and the radiation source position of interest So intersects with z=sz1 (i.e., a plane passing through the reference radiation source position Sb and perpendicular to the z-axis) is "A", and the position coordinates of the intersection point A are (ax,ay,az), then, the relationship between the intersection point A and the reference radiation source position Sb is expressed by Equation (4) below with using the position coordinates (px1,py1) and (px2,py2) of the midpoints C1 and C2 and the distance mz between the detection plane of the detector 14 and the top surface of the imaging table top 4:

$$ax = sx1 - (px2 - px1) \times ((sz1 - mz)/mz)$$

$$ay = sy1 - (py2 - py1) \times ((sz1 - mz)/mz) \quad (4)$$

$$az = sz1$$

On the other hand, the relationship between the intersection point A and the radiation source position of interest So is expressed by Equation (5) below with using the position coordinates (px1,py1) and (px2,py2) of the midpoints C1 and C2 and the distance mz between the detection plane of the detector 14 and the top surface of the imaging table top 4:

$$sx2 = px2 + (ax - px2) \times sz2/az$$

$$sy2 = py2 + (ay - py2) \times sz2/az \quad (5)$$

$$sz2 = az \times (1 - (d2-d1) \times (az-mz)/((d2-d1) \times az + d1 \times mz))$$

Therefore, by substituting the coordinates (ax,ay,az) in Equation (4) into Equation (5), the position coordinates (sx2, sy2,sz2) of the radiation source position of interest So can be expressed with using the position coordinates (sx1,sy1,sz1) of the reference radiation source position Sb. The radiation source position calculating unit 32 uses one of the radiation source positions 51, S2, . . . , and Sn calculated by the computing unit 30 as the reference radiation source position Sb to calculate the relative position coordinates (sx2,sy2,sz2) of the radiation source position of interest So relative to the reference radiation source position Sb according to Equations (4) and (5) above.

It should be noted that, although the distances d1 and d2 between the two marker images and the position coordinates (px1,py1) and (px2,py2) of the midpoints C1 and C2 between the two marker images are used in Equations (4) and (5), position coordinates of one marker image may be used in place of the position coordinates of the midpoint between two marker images. Further, position coordinates of the center point of one marker image and the size of the marker image may be used in place of the position coordinates of the midpoint between the two markers and the distance between the two markers. The reconstruction unit 22 finds a projection position of each point on a slice desired to be reconstructed in the subject 2 onto each image with using the position coordinates of each radiation source position of interest So calculated by the radiation source position calculating unit 32, and adds up pixel values at each projection position to reconstruct the images to generate a tomographic image. Specifically, assuming that coordinates of each point on the slice are (x,y,z), coordinates of the projection position of each point onto the i-th image (i=1 to n) are (ti, si), and the pixel value at the projection position (ti, si) is Pi (ti, si), the tomographic image is generated by calculating a signal value Tz (x,y) of a reconstructed image at each point on the slice according to Equation (6) below:

$$T_z(x, y) = \sum_{i=1}^{n} P_i(t_i, s_i) \qquad (6)$$

$$= \sum_{i=1}^{n} P_i \begin{pmatrix} x * \dfrac{sz_i}{sz_i - z} - sx_i * \dfrac{z}{sz_i - z}, \\ y * \dfrac{sz_i}{sz_i - z} - sy_i * \dfrac{z}{sz_i - z} \end{pmatrix}$$

In Equation (6), the coordinates (sxi,syi,szi) represent position coordinates of the radiation source position, with which the i-th image is obtained, relative to the reference radiation source position Sb.

The X-ray imaging apparatus 10 further includes a control unit 34 for controlling the units of the X-ray imaging apparatus 10. The control unit 34 controls the units of the X-ray imaging apparatus 10 according to instructions fed from the operation unit 24. Further, the control unit 34 controls the X-ray dose applied to the subject 2 based on the X-ray tube 12 according to the tube voltage and tube current of the X-ray tube 12 and the X-ray exposure time stored in the storage unit 28.

Figure 7:
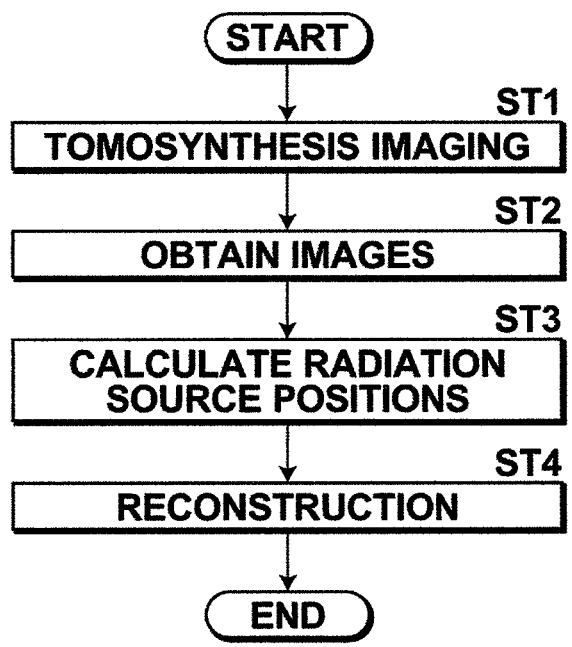
FIG. 7 is a flow chart illustrating a process carried out in the first embodiment.

Next, a process carried out in the first embodiment is described. FIG. 7 is a flow chart illustrating the process carried out in the first embodiment. In this embodiment, tomosynthesis imaging is carried out with moving only the X-ray tube 12 and without moving the detector 14. When the operation unit 24 has received an instruction to start the process fed by the operator, the control unit 38 starts the process to carry out tomosynthesis imaging with moving the X-ray tube 12 (step ST1), and the image obtaining unit 20 obtains a plurality of images (step ST2). Then, the radiation source position calculating unit 32 calculates the positional information of each radiation source position of interest (i.e., each radiation source position other than the reference radiation source position) So relative to the reference radiation source position Sb based on the positions of the markers M1 to M4 and the positional information of the marker images ("calculate radiation source positions" in step ST3). Then, the reconstruction unit 22 reconstructs the images with aligning positions of the object in the subject 2 captured in the images with each other based on the positional information of each radiation source position of interest So relative to the reference radiation source position Sb to generate a tomographic image (step ST4), and the process ends. It should be noted that the thus generated tomographic image is stored in a storage device (not shown), such as a HDD, or sent to an external server via a network.

As described above, according to this embodiment, the positional information of each radiation source position of interest So, which is the object of the position calculation, relative to the reference radiation source position Sb, at which the reference image is obtained, is obtained based on the marker images contained in each of the reference image and the image of interest. Therefore, even when the coordinates of the reference imaging position Sb are unknown, the positional information of each radiation source position of interest Sb relative to the reference imaging position Sb can be obtained. Further, since it is not necessary to use the positional information of the markers and positional relationship between the markers for alignment, the markers can be freely positioned during imaging, thereby increasing freedom of imaging. In addition, during reconstruction, accurate alignment of the images can be achieved with using the reference image obtained at the reference imaging position Sb as the reference, thereby providing a high quality tomographic image.

Figure 8:
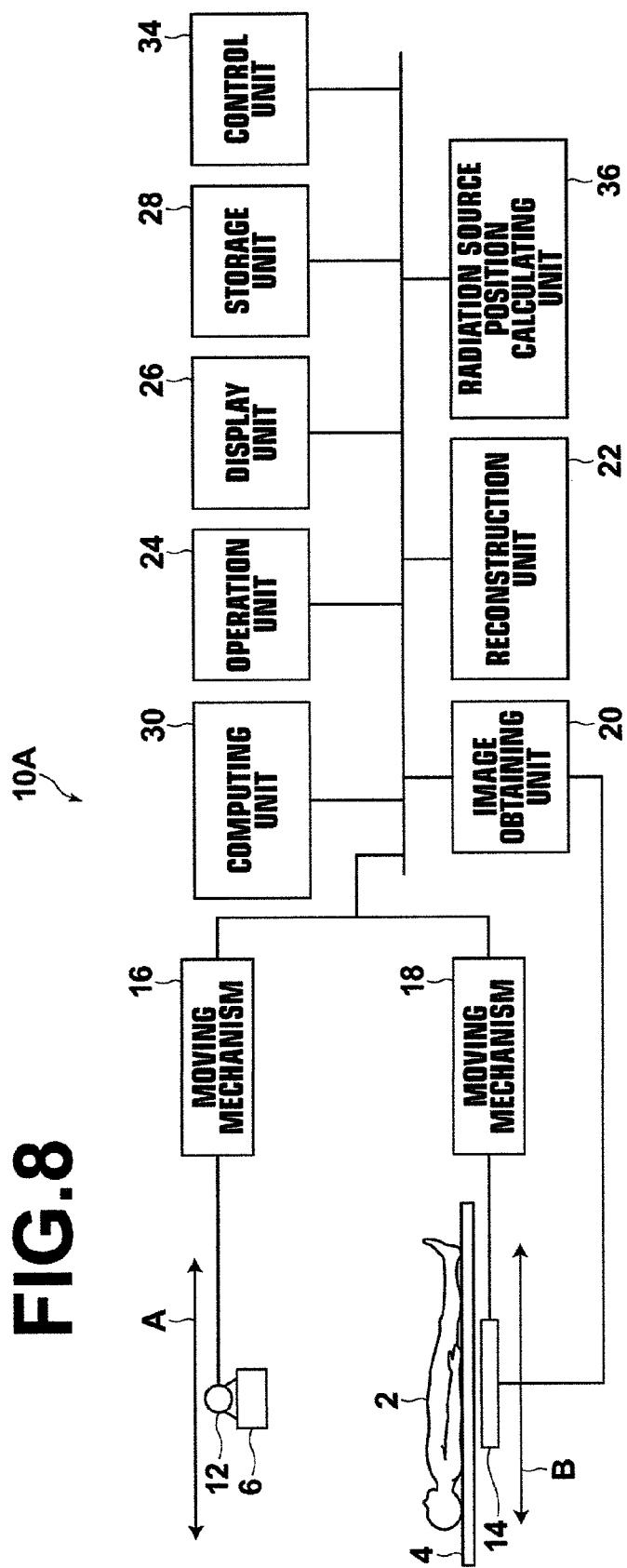
FIG. 8 is a schematic diagram of an X-ray imaging apparatus, to which a radiographic imaging apparatus according to a second embodiment of the invention is applied.
Figure 9:
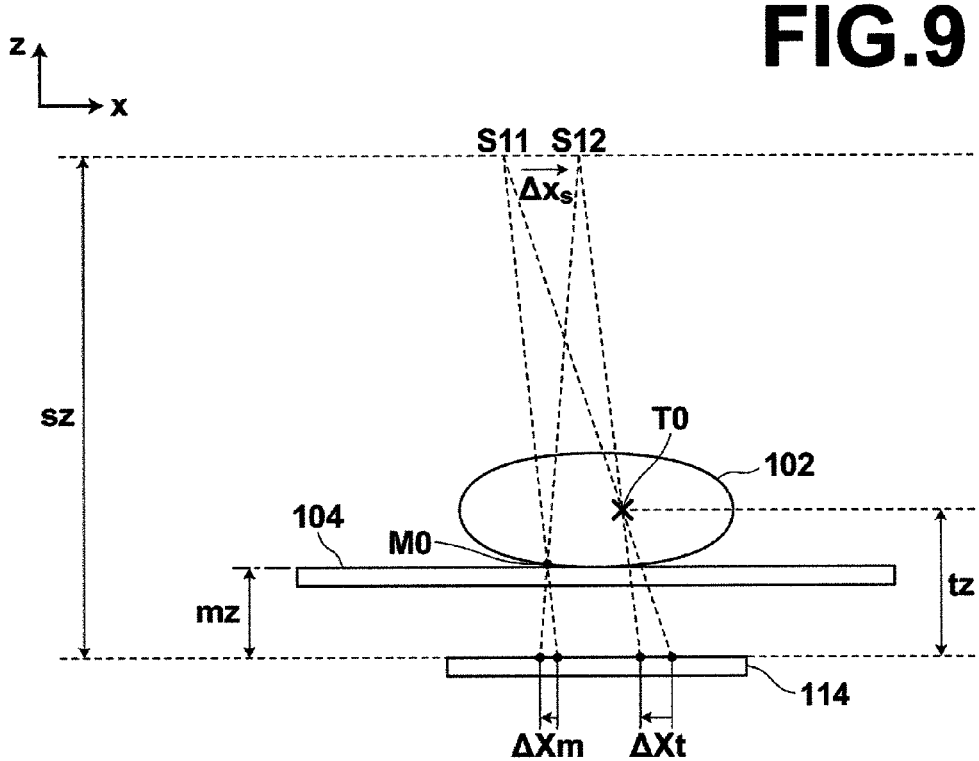
FIG. 9 is a diagram for explaining how alignment is achieved in a conventional technique.

Next, a second embodiment of the invention is described. FIG. 8 is a schematic diagram of an X-ray imaging apparatus, to which a radiographic imaging apparatus according to the second embodiment of the invention is applied. It should be noted that features in the second embodiment which are the same as those in the first embodiment are denoted by the same reference numerals, and detailed descriptions thereof are omitted. The X-ray imaging apparatus 10A according to the second embodiment includes a radiation source position calculating unit 36, which calculates the relative position of each radiation source position of interest So relative to the reference radiation source position Sb in a manner different from that of the first embodiment.

In the case where imaging operations are carried out with using markers, marker images are detected from the obtained images, and the images are aligned with using the marker images contained in the images, as in the first embodiment. However, in actual cases, some of the marker images may be erroneously detected or fail to be detected, and this may results in erroneous position and size detection of the marker images. The calculation of the radiation source positions in the first embodiment assumes that the imaging table top 4, on which the markers are positioned, is parallel to the detection plane of the detector 14. Therefore, if the markers are positioned at different heights, errors may occur during the calculation of each radiation source position of interest according to Equations (4) and (5) described above.

Assuming here that three-dimensional position coordinates of each marker is (mx,my,mz) and position coordinates of each radiation source position is (sx,sy,sz), then, position coordinates (px,py) of each marker image are expressed by Equation (8) below:

$$px=(mx \times sz - sx \times mz)/(sz-mz)$$

$$py=(my \times sz - sy \times mz)/(sz-mz) \quad (8)$$

In the second embodiment, the radiation source position calculating unit 36 optimizes position coordinates (sxi,syi,szi) (i=1 to n) of the radiation source positions and three-dimensional position coordinates (mxj,myj,mzj) (j=1 to J, where J is the number of markers) of the markers to minimize an error E (which will hereinafter be referred to as "projection error") between the position of each marker image calculated according to Equation (8) and actual position coordinates (px',py') of the marker image detected from the image, thereby calculating the positional information of the radiation source positions other than the reference radiation source position Sb relative to the reference radiation source position Sb and the positional information of the markers.

In the second embodiment, the reference radiation source position Sb is the radiation source position at which the first imaging operation is carried out (i=1), and the value calculated by the computing unit 30 is used. The radiation source position calculating unit 36 detects the marker images from the reference image obtained with the reference radiation source position Sb, and calculates, as initial values of the position coordinates of each marker, the position coordinates (mxj,myj,mzj) of each marker from the position of each marker image and the reference radiation source position Sb. Then, the radiation source position calculating unit 36 optimizes the position coordinates (sxi,syi,szi) (i=2 to n) of each radiation source position other than the reference radiation source position Sb and the position coordinates (mxj,myj,mzj) (j=1 to J) of each marker to minimize the projection error. It should be noted that the initial values of the coordinates (sxi,syi,szi) are values calculated by the computing unit 30.

The projection error E of the marker image of a certain marker with respect to the plurality of radiation source positions is expressed by Equation (9) below:

$$E=\Sigma((px-px')^2 + (py-py')^2) \quad (9)$$

The variables in Equation (9) are the position coordinates (sxi,syi,szi) of the radiation source positions and the position coordinates (mxj,myj,mzj) of the marker, according to Equation (8). Therefore, the radiation source position calculating unit 36 optimizes Equation (8) with using a known optimization technique, such as the steepest descent method or the conjugate gradient method, thereby calculating the relative position coordinates of the radiation source positions relative to the reference radiation source position Sb, and the position coordinates of the marker. This provides not only the radiation source positions but also the position coordinates of the marker. Therefore, even if some of the markers are erroneously detected or fail to be detected, the position coordinates of the markers can be obtained in a relatively stable manner.

It should be noted that the relative position coordinates of each radiation source position relative to the reference radiation source position Sb and the position coordinates of each marker may be calculated by repeating first calculating the position coordinates (sxi,syi,szi) of each radiation source position to minimize the projection error, and then, calculating the position coordinates (mxj,myj,mzj) of each marker to minimize the projection error. In contrast, the relative position coordinates of each radiation source position relative to the reference radiation source position Sb and the position coordinates of each marker may be calculated by repeating first calculating the position coordinates (mxj,myj,mzj) of each marker to minimize the projection error, and then, calculating the position coordinates (sxi,syi,szi) of each radiation source positions to minimize the projection error.

In either case, the number of repetition may be set in advance, and the process may end when the number of repetition has reached the set number of repetition. Then, the relative position coordinates of each radiation source position relative to the reference radiation source position Sb and the position coordinates of each marker found at that time may be outputted. Alternatively, the process may end when the projection error has converged and further optimization will not reduce the projection error any more, or when the projection error has become equal to or less than a predetermined threshold. Then, the relative position coordinates of each radiation source position relative to the reference radiation source position Sb and the position coordinates of each marker found at that time may be outputted.

The thus calculated radiation source positions may be smoothed, as necessary, with using spline interpolation, or the like.

It should be noted that, although the radiation source position with which the first imaging operation is carried out is used as the reference radiation source position Sb in the above-described first and second embodiments, this is not intended to limit the invention. For example, a radiation source position that is substantially straight in front of the detector 14 may be used as the reference radiation source position.

Further, although only the X-ray tube 12 is moved in the above-described first and second embodiments, the X-ray tube 12 and the detector 14 may be moved synchronously. In this case, it is necessary to calculate the radiation source positions with reflecting, on the positions of the detected marker images, positional information of the detector 14 corresponding to each radiation source position.

Still further, although the tomosynthesis imaging is carried out with the subject in the supine position being placed on the imaging table in the above-described first and second embodiments, the present invention is also applicable to the case where the tomosynthesis imaging is carried out with using an imaging table for the upright position.

Yet further, although the radiation source positions are calculated at the imaging apparatus which carries out tomosynthesis imaging in the above-described first and second embodiments, the present invention is applicable to any imaging apparatus which obtains a plurality of images by imaging a subject with a plurality of radiation source positions. For example, the present invention is applicable to a transmission imaging apparatus that carries out transmission imaging with using a contrast agent (such as an imaging apparatus for gastroscopy using barium), a mammography imaging apparatus, or an imaging apparatus for imaging a long subject, such as the spine, with moving the detector and the X-ray tube.

Further, although the trajectories of the X-ray tube 12 and the detector 14 are a straight line or a circular arc in the above-described first and second embodiments, the present invention is also applicable to a precession trajectory.

What is claimed is:

1. A radiographic imaging apparatus comprising:
a radiation source for applying radiation to a subject and at least one marker;
detecting means for detecting the radiation transmitted through the subject;
image obtaining means for moving the radiation source relative to the detecting means, applying the radiation to the subject from a plurality of radiation source positions provided by the movement of the radiation source, and obtaining a plurality of images corresponding respectively to the radiation source positions; and
radiation source position obtaining means for obtaining positional information of each radiation source position of interest relative to a reference radiation source position, the radiation source position of interest being one of the radiation source positions other than the reference radiation source positions, based on at least one marker image contained in each of a reference image obtained with the reference radiation source position and an image of interest obtained with the radiation source position of interest,
wherein the radiation source position obtaining means obtains the positional information of each radiation source position of interest by determining an optimal solution of the positional information of the radiation source position of interest to minimize an error between a position of the at least one marker image contained in each of the reference image and the image of interest and a projection position of the marker image calculated from a relationship among the reference radiation source position, the radiation source position of interest and a position of the marker.

2. The radiographic imaging apparatus as claimed in claim 1, wherein the radiation source position obtaining means determines the optimal solution of the positional information of each radiation source position of interest by repeating optimization of the positional information of the radiation source position of interest and optimization of positional information of the marker.

3. The radiographic imaging apparatus as claimed in claim 1, further comprising image reconstructing means for generating a tomographic image of the subject with using the reference radiation source position and the positional information of each radiation source position of interest.

4. A radiographic imaging method for use with a radiographic imaging apparatus including a radiation source for applying radiation to a subject and at least one marker, detecting means for detecting the radiation transmitted through the subject, and image obtaining means for moving the radiation source relative to the detecting means, applying the radiation to the subject from a plurality of radiation source positions provided by the movement of the radiation source, and obtaining a plurality of images corresponding respectively to the radiation source positions, the method comprising:
obtaining positional information of each radiation source position of interest relative to a reference radiation source position, the radiation source position of interest being one of the radiation source positions other than the reference radiation source position among the radiation source positions, based on at least one marker image contained in each of a reference image obtained with the reference radiation source position and an image of interest obtained with the radiation source position of interest,
wherein the obtaining step includes obtaining the positional information of each radiation source position of interest by determining an optimal solution of the positional information of the radiation source position of interest to minimize an error between a position of the at least one marker image contained in each of the reference image and the image of interest and a projection position of the marker image calculated from a relationship among the reference radiation source position, the radiation source position of interest and a position of the marker.

5. A Computer-readable recording medium containing a program for causing a computer to carry out a radiographic imaging method for use with a radiographic imaging apparatus including a radiation source for applying radiation to a subject and at least one marker, detecting means for detecting the radiation transmitted through the subject, and image obtaining means for moving the radiation source relative to the detecting means, applying the radiation to the subject from a plurality of radiation source positions provided by the movement of the radiation source, and obtaining a plurality of images corresponding respectively to the radiation source positions, the program causing the computer to carry out the procedure of:

obtaining positional information of each radiation source position of interest relative to a reference radiation source position, the radiation source position of interest being one of the radiation source positions other than the reference radiation source position among the radiation source positions, based on at least one marker image contained in each of a reference image obtained with the reference radiation source position and an image of interest obtained with the radiation source position of interest, wherein the obtaining includes obtaining the positional information of each radiation source position of interest by determining an optimal solution of the positional information of the radiation source position of interest to minimize an error between a position of the at least one marker image contained in each of the reference image and the image of interest and a projection position of the marker image calculated from a relationship among the reference radiation source position, the radiation source position of interest and a position of the marker.

* * * * *